United States Patent
Majeed et al.

(10) Patent No.: US 7,521,580 B1
(45) Date of Patent: Apr. 21, 2009

(54) NON-CYTOTOXIC SYNTHETIC ANALOGUES OF (1E, 6E)-1, 7-BIS (4-HYDROXY-3-METHOXYPHENYL)-1, 6-HEPTADIENE-3, 5-DIONE AND THERAPEUTIC APPLICATIONS THEREOF IN CYSTIC FIBROSIS

(75) Inventors: Muhammed Majeed, Piscataway, NJ (US); Rajinder Kumar Bammi, Bangalore (IN); Natarajan Sankaran, Bangalore (IN); Subbalakshmi Prakash, Piscataway, NJ (US); Kalyanam Nagabhushanam, Piscataway, NJ (US); Samuel Manoharan Thomas, Bangalore (IN); Susmitha Anand, Bangalore (IN); Geetha Kanhangad-Gangadharan, Bangalore (IN)

(73) Assignee: Sami Labs Ltd., Bangalore (IN)

( * ) Notice: Subject to any disclaimer, the term of this patent is extended or adjusted under 35 U.S.C. 154(b) by 0 days.

(21) Appl. No.: 12/032,955

(22) Filed: Feb. 18, 2008

(51) Int. Cl.
*C07C 49/203* (2006.01)
*C07C 49/215* (2006.01)
*A61K 31/12* (2006.01)

(52) U.S. Cl. ..................... 568/325; 514/679
(58) Field of Classification Search .............. 568/325; 514/679

See application file for complete search history.

(56) References Cited

OTHER PUBLICATIONS

Egan et al. Circumen, A Major Constituent of Tumeric, Corrects Cystic Fibrosis Defects. Science. 2004, Apr. 2003, 304 (5670), pp. 600-602.*

* cited by examiner

*Primary Examiner*—Sikarl A Witherspoon

(57) ABSTRACT

Disclosed are novel, synthetic analogues of (1E,6E)-1,7-Bis (4-hydroxy-3-methoxyphenyl)-1,6-heptadiene-3,5-dione and the therapeutic applications for cystic fibrosis thereof in correcting altered CFTR trafficking and the associated impaired chloride ($Cl^-$) ion transport. Introduction of branched-alkyl groups ortho to the phenolic groups gave rise to clinical compounds with vastly improved trafficking of delF508CFTR and with no cytotoxicity.

8 Claims, 4 Drawing Sheets log[(1E,6E)-1,7-Bis(3,5-di-tert-butyl-4-hydroxyphenyl)-1,6-heptadiene-3,5-dione]

NON-CYTOTOXIC SYNTHETIC ANALOGUES OF (1E, 6E)-1, 7-BIS (4-HYDROXY-3-METHOXYPHENYL)-1, 6-HEPTADIENE-3, 5-DIONE AND THERAPEUTIC APPLICATIONS THEREOF IN CYSTIC FIBROSIS

BACKGROUND OF THE INVENTION

The present invention in general relates to the interventional molecules for cystic fibrosis. More specifically, the present invention relates to novel, non-cytotoxic synthetic analogues of (1E,6E)-1,7-Bis(4-hydroxy-3-methoxyphenyl)-1,6-heptadiene-3,5-dione and therapeutic applications thereof in correcting altered CFTR trafficking and the associated impaired chloride (Cl⁻) ion transport occurring in cystic fibrosis cells through a calcium dependant mechanism of action.

DESCRIPTION OF PRIOR ART (1E,6E)-1,7-Bis(4-hydroxy-3-methoxyphenyl)-1,6-heptadiene-3,5-dione as interventional molecules for cystic fibrosis has been discussed in prior art. Some important references have been elucidated herein below.

Egan et al. described the role of Curcumin, a major constituent of turmeric, in correcting cystic fibrosis defects. (Science. 2004 Apr. 23; 304(5670):600-2)

Song, et al. provided evidence against the rescue of defective DeltaF508-CFTR cellular processing by curcumin in cell culture and mouse models. (J Biol Chem. 2004 Sep. 24; 279(39):40629-33. Davis et al, (Trends Mol Med. 2004 October; 10(10):473-5); Croft et al. (Gastroenterology. 2004 November; 127(5)); and Emanuele, et al. (Med Hypotheses. 2007; 69(1):222-3) reviewed the beneficial role of curcumin in cystic fibrosis.

Berger et al. reported that Curcumin stimulates cystic fibrosis transmembrane conductance regulator Cl— channel activity (J Biol Chem. 2005 Feb. 18; 280(7):5221-6); Lipecka et al. described the involvement of keratin 18 network in the rescue of DeltaF508-CFTR (cystic fibrosis transmembrane conductance regulator) by curcumin (Pharmacol Exp Ther. 2006 May; 317(2):500-5. Epub 2006).

Harada et al. showed that curcumin enhances cystic fibrosis transmembrane regulator expression by down-regulating calreticulin (Biochem Biophys Res Commun. 2007 Feb. 9; 353(2):351-6); while Wang et al. postulated that curcumin opens cystic fibrosis transmembrane conductance regulator channels by a novel mechanism that requires neither ATP binding nor dimerization of the nucleotide-binding domains (J Biol Chem. 2007 Feb. 16; 282(7):4533-44).

However, the cell cytotoxicity of (1E,6E)-1,7-Bis(4-hydroxy-3-methoxyphenyl)-1,6-heptadiene-3,5-dione and its ability to non-specifically induce both mutated and wild type CFTR (demonstrated herein by the inventors themselves) has led to speculations on its therapeutic potential for cystic fibrosis. Surprisingly, the present inventors have found synthetic analogues of (1E,6E)-1,7-Bis(4-hydroxy-3-methoxyphenyl)-1,6-heptadiene-3,5-Dione are suitable alternatives for cystic fibrosis therapy by virtue of their reduced cell cytotoxicity and their selective therapeutic action in correcting altered CFTR trafficking and the associated impaired chloride (Cl⁻) ion transport in CF cells with insignificant effect on wild type CFTR.

It is thus the principle object of the present invention to disclose novel, non-cytotoxic synthetic analogues of (1E, 6E)-1,7-bis(4-hydroxy-3-methoxyphenyl)-1,6-heptadiene-3,5-dione which based on their chemistry offer substantial therapeutic potential thereof for cystic fibrosis by correcting altered CFTR trafficking and the associated chloride (Cl⁻) ion transport in CF cells.

The present invention fulfills the principle objective and provides further related advantages.

SUMMARY OF THE INVENTION

The present invention relates to novel, non-cytotoxic synthetic analogues of (1E,6E)-1,7-Bis(4-hydroxy-3-methoxyphenyl)-1,6-heptadiene-3,5-dione and therapeutic applications thereof in correcting altered CFTR trafficking and the associated impaired chloride (Cl—) ion transport occurring in cystic fibrosis cells through a calcium dependant mechanism of action. The present invention is based on the observation that synthetic analogues of (1E,6E)-1,7-Bis(4-hydroxy-3-methoxyphenyl)-1,6-heptadiene-3,5-dione in which the phenolic hydroxyl is flanked by alkyl groups which are branched at α-carbon or at β-carbon are very active as interventional molecules for correcting the altered CFTR trafficking and the associated defective chloride ion (Cl–) transport in CF cells. Accordingly the present invention discloses pharmacological interventional molecules for cystic fibrosis therapy represented by the general formula (STR#1) wherein R2=R4 may include functional groups, one selected from tertiary-butyl group, isopropyl group, 1-methylpropyl group, isooctyl group, 2-methylpropyl group, or 2-ethylhexyl group.

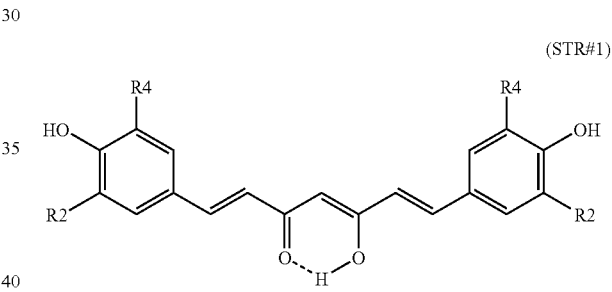

(STR#1)

Other features and advantages of the present invention will become apparent from the following more detailed description, taken in conjunction with the accompanying drawings, which illustrate, by way of example, the principle of the invention.

DESCRIPTION OF THE PREFERRED EMBODIMENT

Figure 1A:
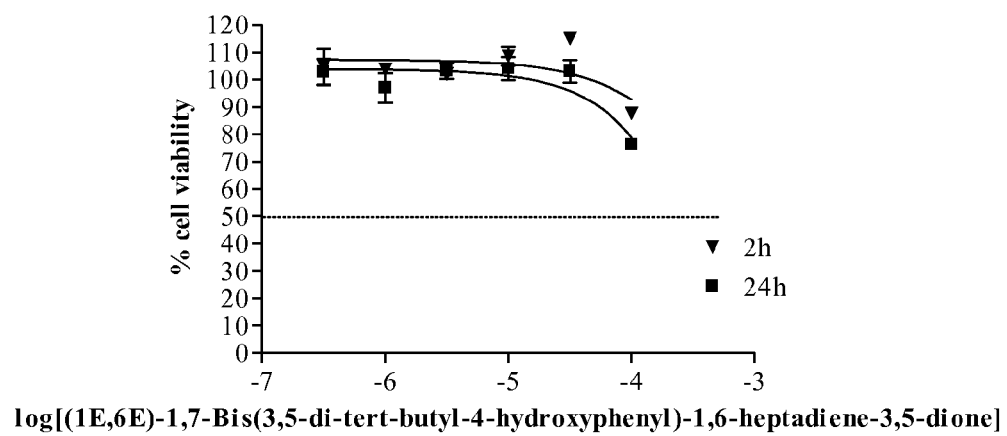
FIG. 1 shows the comparative concentration-response curves of cell viability with increasing concentrations of (1E, 6E)-1,7-Bis(4-hydroxy-3-methoxyphenyl)-1,6-heptadiene-3,5-dione and (1E,6E)-1,7-Bis(3,5-di-tert-butyl-4-hydroxyphenyl)-1,6-heptadiene-3,5-dione (representative example of the molecules disclosed the present invention) for 2 or 24 hours of incubation.
Figure 1B:
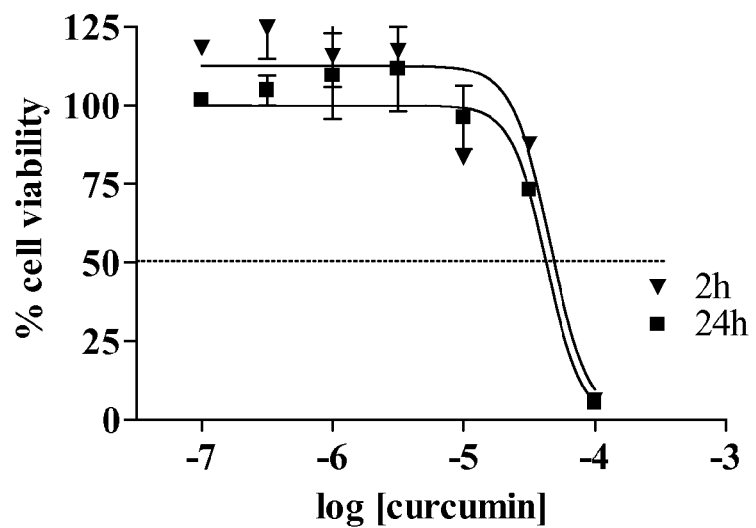

In the most preferred embodiment, the present invention discloses pharmacological interventional molecules for cystic fibrosis therapy, said molecules being represented by the general formula (STR#1), wherein the phenolic hydroxyl group is flanked by alkyl groups branched at α-carbon position or β-carbon position.

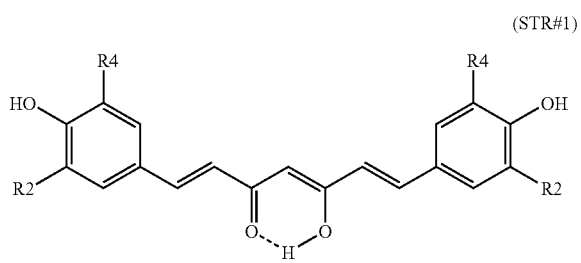

(STR#1)

More preferably, the present invention includes pharmacological intervention molecules for cystic fibrosis therapy, wherein R2=R4 may include one functional group selected from the isopropyl group, 1-methylpropyl group, isooctyl group, 2-methylpropyl group and 2-ethylhexyl group.

The potential therapeutic value of the molecules disclosed in the present invention for cystic fibrosis may be understood through examples elucidated herein below.

EXAMPLE 1

Preparation of (1E,6E)-1,7-Bis(3,5-di-tert-butyl-4-hydroxyphenyl)-1,6-heptadiene-3,5-dione Representative of the Molecules of the Present Invention Acetylacetone (2.0 g, 0.02 mol) and boric oxide (0.98 g, 0.014 mol) are mixed in dry dichloromethane (30 mL) in a 100 mL round bottomed flask and stirred at room temperature for one hour under dry condition. Tri-sec-butylborate (9.2 g, 0.04 mol) is added to this mixture and stirred for 5 min. The aromatic aldehyde (1a-f) (0.04 mol) is dissolved in dry dimethylformamide/chloroform/dichloromethane or a mixture of these solvents (~50-100 mL) in a three necked 250 mL round bottomed flask fitted with a mechanical agitator and calcium chloride drying tube. Tri-sec-butylborate (9.2 g, 0.04 mol) is added and stirred for 5 min. Acetylacetone-boric oxide complex prepared above is added and stirred for 10 min. n-Butylamine (0.3 g, 0.004 mol) dissolved in dichloromethane (3.0 mL) is dropped in over a period of 30 min and stirred at room temperature over night (~24 h). This is poured into 100 mL of 5% aq. acetic acid at 50° C. and stirred for an hour. The precipitated crude curcuminoid is filtered, dried in vacuo and crystallized from isopropyl alcohol to get the pure curcuminoid.

Properties of (1E,6E)-1,7-Bis(3,5-di-tert-butyl-4-hydroxyphenyl)-1,6-heptadiene-3,5-dione (1E,6E)-1,7-Bis(3,5-di-tert-butyl-4-hydroxyphenyl)-1,6-heptadiene-3,5-dione is a yellow powder (yield 66%), m.p. 192.0-196.0° C., 98% HPLC purity.

1H NMR (CDCl$_3$, 300 MHz): δ 1.467 (s, 36H), 5.533 (s, 2H, —OH), 5.870 (s, 1H), 6.495 (d, J=15.6 Hz, 2H), 7.405 (s, 4H), 7.623 (d, J=15.6 Hz, 2H).

13C NMR (CDCl$_3$, 75 MHz): δ 30.403, 34.604, 101.166, 121.347, 125.746, 126.640, 136.595, 141.617, 156.307, 183.665, 192.161.

LC-MS: m/e 533 (M++1).

Measurement of Cellular Cytotoxicity

The cytotoxicity of (1E,6E)-1,7-Bis(3,5-di-tert-butyl-4-hydroxyphenyl)-1,6-heptadiene-3,5-dione (representative of the molecules disclosed in the present invention) was assessed by MTT assay [[3-(4,5-dimethylthiazol-2-yl)-2,5-diphenyl tetrazolium bromide, measuring cellular dehydrogenase activity on CHO-CFTR-wt cell lines. The test is based on the principle that water soluble tetrazolium yellow salt MTT (Sigma®) is converted on purple formazan by mitochondrial dehydrogenase. Cells were grown to confluency in 96-well plates. After incubation with the test compound for 2 or 24 hours, at 37° C., 10 μM of MTT (5 mg/ml) was added. After 4 h of incubation, culture medium was removed and 100 μl of DMSO per well added to solubilise formazan crystals. Optical density (OD) was measured at 570 nm and subtracted to these measured at 630 nm. The amount of purple formazan produced by treated cells is compared with these of untreated control cells (vehicle), dose-response curves were derived using GraphPad Software. The results of the MTT assay are shown in Table I.

TABLE I

| Compoun TC$_{50}$ (μM) | Curcumin | (1E,6E)-1,7-Bis (3,5-di-tert-butyl-4-hydroxyphenyl heptadiene-3,5-dione |
|---|---|---|
| 2 h incubatio | 50.1 ± 1.1 | >100 |
| 24 h incubatio | 42.7 ± 1.0 | >100 |

Evaluation of F508del-CFTR Chloride Channel Activity

The human nasal airway epithelial cells JME/CF15 were cultured in 24-well plates to 90% confluence. (1E,6E)-1,7-Bis(3,5-di-tert-butyl-4-hydroxyphenyl)-1,6-heptadiene-3,5-dione was added at 100 μM for 2 hours, at 37° C., 5% CO2. After incubation, chloride channel activity was assayed by measuring the rate of radio labelled iodide (125 l) efflux using liquid handling robots. The compound was tested in quadruplicate. Cells were incubated in physiologic solution containing 1 μM Kl and 1 μCi Na 125 l/ml during 1 h at 37° C. Extra cellular 125 l was removed by 3 washes of cells, and the loss of intracellular 125 l is determined by removing the medium with physiological solution every minute for up to 9 min 6. A cocktail of forskolin (10 μM) plus genistein (30 μM) was added at the third minute to stimulate F508del-CFTR chloride channel activity. Statistics and curves were derived at using Graph Pad Software.

Figure 2:
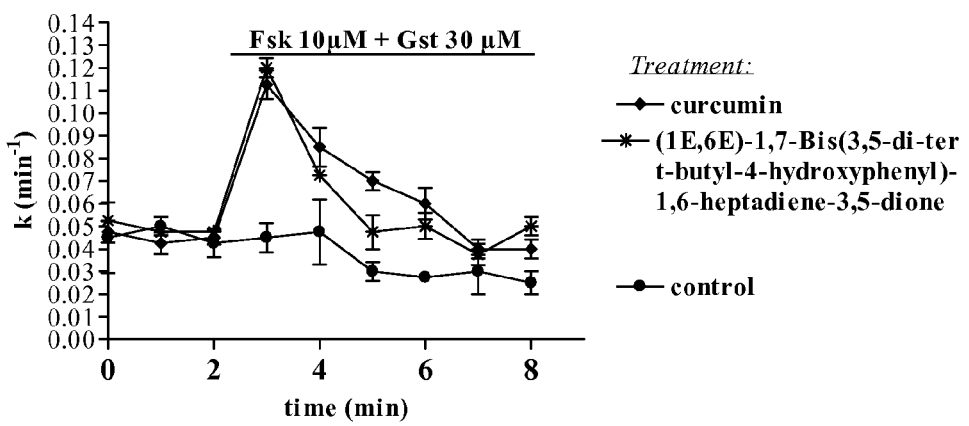
FIGS. 2a and 2b shows the graphical representation of the iodide efflux STIMULATION BY (1E,6E)-1,7-Bis(4-hydroxy-3-methoxyphenyl)-1,6-heptadiene-3,5-dione and (1E, 6E)-1,7-Bis(3,5-di-tert-butyl-4-hydroxyphenyl)-1,6-heptadiene-3,5-dione (representative example of the molecules disclosed the present invention).
Figure 2B:
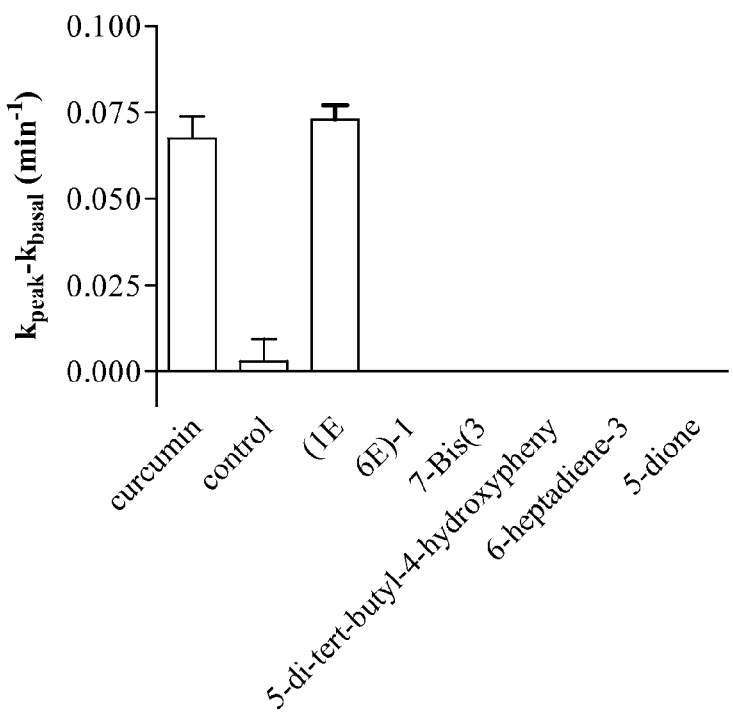

The results (FIGS. 2a and 2b) demonstrated that (1E,6E)-1,7-Bis(3,5-di-tert-butyl-4-hydroxyphenyl)-1,6-heptadiene-3,5-dione was able to restore the F508del-CFTR protein at the plasma membrane of CF cells.

Evaluation of Wild Type CFTR Chloride Channel Activity

Figure 3:
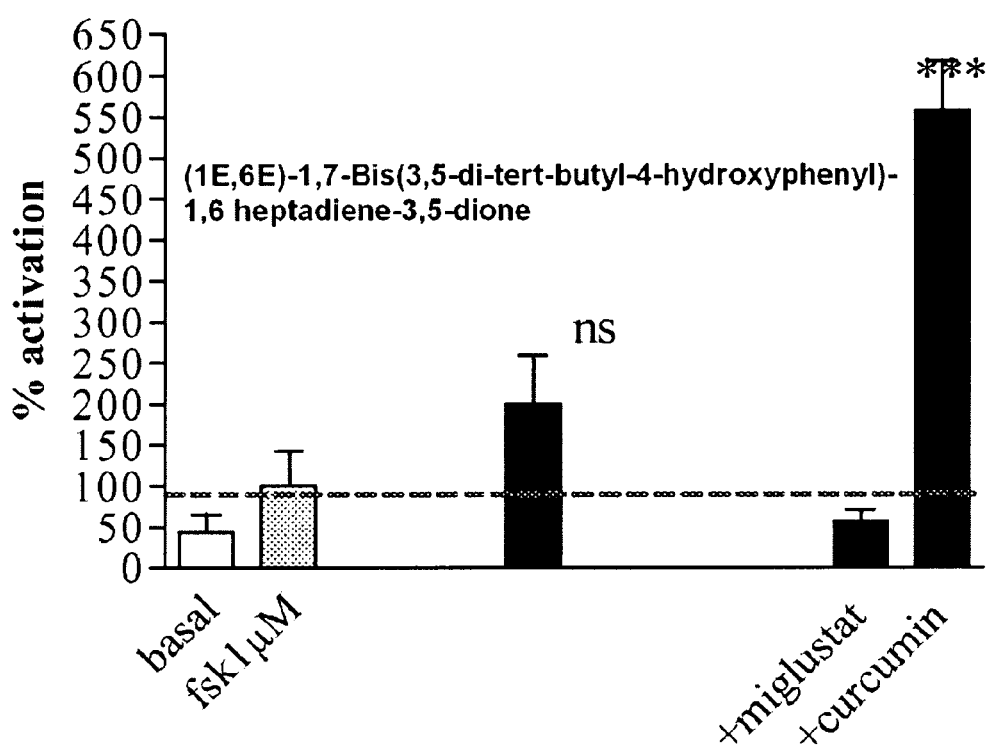
FIG. 3 shows the graphical representation of the comparative abilities of (1E,6E)-1,7-Bis(4-hydroxy-3-methoxyphenyl)-1,6-heptadiene-3,5-dione and (1E,6E)-1,7-Bis(3,5-di-tert-butyl-4-hydroxyphenyl)-1,6-heptadiene-3,5-dione (representative example of the molecules disclosed the present invention) to activate wild type CFTR chloride channel activation.
Figure 4A:
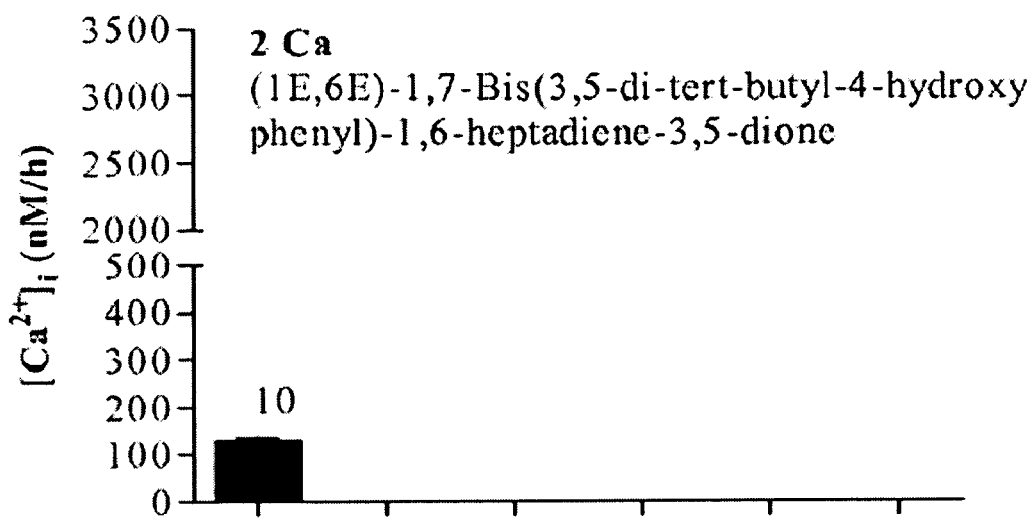
FIGS. 4a and 4b show the graphical representation intracellular calcium mobilization activities of (1E,6E)-1,7-Bis(3,5-di-tert-butyl-4-hydroxyphenyl)-1,6-heptadiene-3,5-dione (representative example of the molecules disclosed the present invention) in the presence of extracellular 2 mM $Ca^{2+}$ and 0 mM $Ca^{2+}$.
Figure 4B:
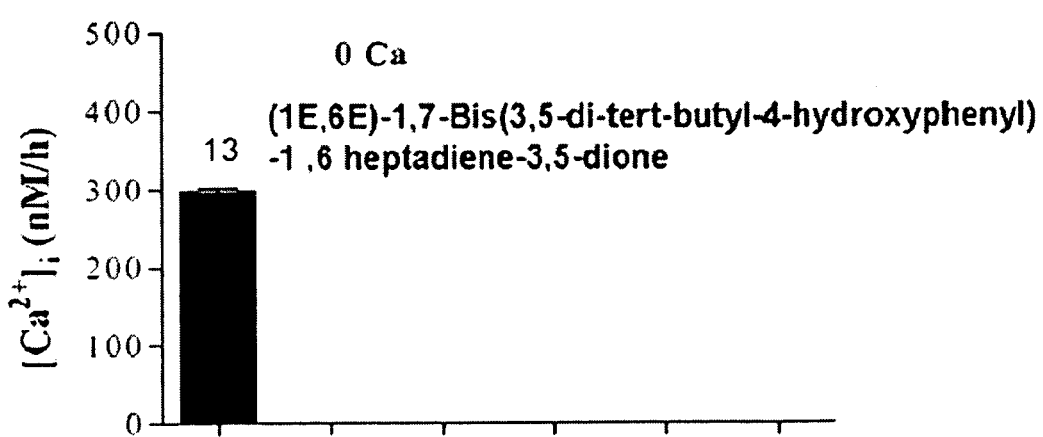

To test the potency to stimulate wt-CFTR channel activity, CHO-CFTR-wt cells were cultured in 24-well plates to 90% confluence. Iodide efflux experiments were carried as described above. (1E,6E)-1,7-Bis(3,5-di-tert-butyl-4-hydroxyphenyl)-1,6-heptadiene-3,5-dione was added in the third minute in the presence or absence of Forskolin (1 μM). The compound was tested in acute (no incubation) at 100 μM in presence of Forskolin 1 μM. Data was normalized as % of activation, 100% corresponding to the amplitude of response recorded with Fsk1 μM alone. The test results showed that (1E,6E)-1,7-Bis(3,5-di-tert-butyl-4-hydroxyphenyl)-1,6-heptadiene-3,5-dione (FIG. 3) showed insignificant wild-type CFTR chloride channel activity.

Calcium Mobilization

A number of epithelial chloride channels are calcium dependent. Therefore molecules which increase cytosolic calcium release or reduce calcium re-uptake by the intracellular stores may be beneficial to increase chloride secretion via a calcium-regulated chloride signaling pathway. Alternatively, a decrease in the activity calcium dependant proteins playing a vital role in retaining misfolded F508-CFTR in the ER may also seem a promising strategy in cystic fibrosis therapy. Altering intraluminal ER calcium with thapsigargin allowed F508-CFTR to be released from the ER while functioning at the apical membrane in CFPAC-1 cells (Egan M E, Cahill P A, Ambrose C A, Pappoe L, Giebel J P, Caplan M. Small molecule approach to increasing F508-CFTR surface expression in CF epithelial cells. Pediatr Pulmonol 2000; 19:242.) To demonstrate, if the compounds of the present invention involve an increase in cytosolic calcium levels, the under said experimental protocols were performed.

JME/CF15 cells were loaded with 3 μM Fluo-4 acetoxymethyl (AM)ester for 20 min at room temperature in buffer solution containing: (in mM) 130 NaCl, 5.4 KCl, 2.5 CaCl2, 0.8 MgCl2, 5.6 glucose, 10 Hepes, pH 7.4 adjusted with Tris base), rinsed and allowed to equilibrate for 5-10 min. Ca2+ activity was recorded by confocal laser scanning microscopy using Bio-Rad MRC 1024 equipped with 15 mW Ar/Kr gas laser (Hemel Hempstead, UK). Maximal resolution was obtained with Olympus plan apo X60 oil, 1.4 NA, objective lens. Fluorescence signal collection was performed through the control software Lasersharp 3.2 (Bio-Rad). The resolution time was 30 s for the protocol in which cells are incubated 2 h in the presence of (1E,6E)-1,7-Bis(3,5-di-tert-butyl-4-hydroxyphenyl)-1,6-heptadiene-3,5-dione. All the experiments were performed at minimum on two different cell passages. The protocol used to show intracellular calcium mobilization consists in the measurement of the calcium mobilization during 2 h of treatment with test compound (100 μM), a period corresponding to the duration of the treatment necessary to rescue F508del-CFTR at the plasma membrane.

The results showed that in the absence of extra cellular calcium (1E,6E)-1,7-Bis(3,5-di-tert-butyl-4-hydroxyphenyl)-1,6-heptadiene-3,5-dione induced intracellular mobilization of $Ca^{2+}$. Thus (1E,6E)-1,7-Bis(3,5-di-tert-butyl-4-hydroxyphenyl)-1,6-heptadiene-3,5-dione is a potential candidate to rescue the F508del-CFTR protein at the plasma membrane by a calcium-dependent mechanism of action.

The reason for the enhanced therapeutic activity could be assigned to the decreased acidity of the phenolic hydroxyl in the compounds disclosed in the present invention. The increased hydrophobicity of these compounds could also be important in therapeutic activity towards cystic fibrosis. Notwithstanding such theory, these compounds are useful in correcting the function of the F508del-CFTR protein thus offering a therapy for cystic fibrosis.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A pharmacological interventional molecule for cystic fibrosis therapy represented by the general formula (STR#1), wherein the phenolic hydroxyl group is flanked by alkyl groups branched at α-carbon position,

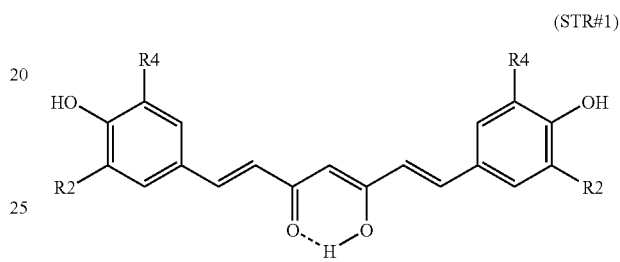

(STR#1)

2. The molecule according to claim 1, wherein R2=R4=tert-butyl group.

3. The molecule according to claim 1, wherein R2=R4=isopropyl group.

4. The molecule according to claim 1, wherein R2=R4=1-methylpropyl group.

5. A pharmacological interventional molecule for cystic fibrosis therapy represented by the general formula (STR#1), wherein the phenolic hydroxyl group is flanked by alkyl groups branched at β-carbon position,

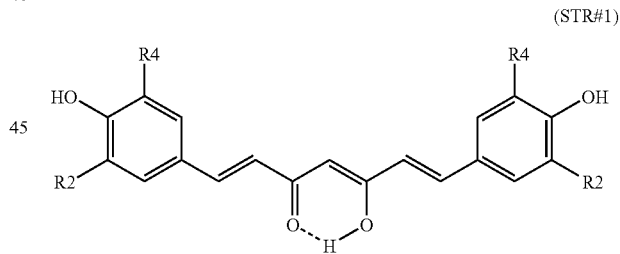

(STR#1)

6. The molecule according to claim 5, wherein R2=R4=isooctyl group.

7. The molecule according to claim 5, wherein R2=R4=2-methylpropyl group.

8. The molecule according to claim 5, wherein R2=R4=2-ethylhexyl group.

* * * * *